United States Patent [19]

Mingrone

[11] Patent Number: 5,272,177
[45] Date of Patent: Dec. 21, 1993

[54] USE OF SEBACIC ACID AND DERIVATIVES THEREOF IN ENTERAL AND PARENTERAL NUTRITION AND PHARMACEUTICAL COMPOSITIONS CONTAINING SAID COMPOUNDS

[75] Inventor: Geltrude Mingrone, Rome, Italy

[73] Assignee: Sigma-Tau Industrie Farmaceutiche Riunite S.p.A., Rome, Italy

[21] Appl. No.: 820,875

[22] PCT Filed: Sep. 14, 1990

[86] PCT No.: PCT/IT90/00073
§ 371 Date: Jan. 29, 1992
§ 102(e) Date: Jan. 29, 1992

[87] PCT Pub. No.: WO91/01963
PCT Pub. Date: Feb. 21, 1991

[30] Foreign Application Priority Data

Jul. 31, 1989 [IT] Italy .................. 48255 A/89

[51] Int. Cl.$^5$ .................. A61K 31/23; A61K 31/19
[52] U.S. Cl. .................. 514/552; 514/574
[58] Field of Search .................. 514/574, 552

[56] References Cited

U.S. PATENT DOCUMENTS 4,386,104  5/1983  Nazzaro-Porro .................. 514/574
4,885,282 12/1989  Thornfeldt .................. 514/574

FOREIGN PATENT DOCUMENTS 0121036 10/1984  European Pat. Off. .
8909594 10/1989  World Int. Prop. O. .

OTHER PUBLICATIONS

Biochimica et Biophysica Acta, vol. 876, No. 3, 1986; Elsevier Science Publishers B. V., (Amsterdam, NL), S. Kolvraa et al.: "In vitro studies on the oxidation of medium-chain dicarboxylic acids in rat liver", pp. 515–525.

Izv. Akad. Nauk.SSSR, Ser. Khim. No. 6, 1965, (SU), K. A. Andrianov et al.: "Synthesis of glycerol derivatives of oligomers with functional groups at the ends of molecules", pp. 1022–1025.

Patent Abstracts of Japan, vol. 10, No. 377 (c-392) (2434) Dec. 16, 1986, & JP, A, 61171417 (Wakunaga Seiyaku K.K.) Aug. 2, 1986.

Biochimica et Biophysica Acta, vol. 710, 1982; Elsevier Biomedical Press, (Amsterdam, NL), P. B. Mortensen et al.: "The biological origin of ketotic dicarboxylic aciduia. II. In vivo and in vitro investigations of the beta-oxidation of $C_8$–$C_{16}$–dicarbodiabetic rats", pp. 477–484.

Quarterly Journal of Experimental Physiology, vol. 73, No. 2, 1988; (GB), G. Mingrone et al.: "Influence of sodium salts of saturated medium chain length ($C_6$,$C_9$,$C_{10}$, and $C_{12}$) dicarboxylic acids on the uterine horn of rat in vitro", pp. 153–162.

Primary Examiner—Frederick E. Waddell
Assistant Examiner—Raymond J. Henley, III
Attorney, Agent, or Firm—Oblon, Spivak, McClelland, Maier & Neustadt

[57] ABSTRACT

Sebacic acid and the pharmacologically acceptable derivatives thereof, such as the novel compounds sodium sebacate and potassium sebacate, the sebacic acid triglyceride and the sodium and potassium salts of the triglyceride are useful for manufacturing pharmaceutical compositions suitable for the enteral and parenteral nutrition.

8 Claims, No Drawings

USE OF SEBACIC ACID AND DERIVATIVES THEREOF IN ENTERAL AND PARENTERAL NUTRITION AND PHARMACEUTICAL COMPOSITIONS CONTAINING SAID COMPOUNDS

The present invention relates to the use of sebacic acid and pharmacologically acceptable sebacic acid derivatives in enteral and parenteral nutrition.

According to the present invention, by "pharmacologically acceptable sebacic acid derivatives" the following compounds are meant: the pharmacologically acceptable salts, particularly the alkaline metal salts, preferably the sodium and potassium salts, the sebacic acid triglyceride and the pharmacologically acceptable salts thereof, preferably the sodium and potassium salts. The sodium and potassium salts of the sebacic acid triglycerides are novel compounds.

In clinical practice, whereas lipid emulsions of triglycerides of long chain monocarboxylic fatty acids have been in general use for total parenteral nutrition for a number of years, only recently the use of some medium chain triglycerides has met with satisfactory results. However, these emulsions suffer from serious drawbacks. Indeed, in some frequently occurring pathological conditions, such as sepsis, conflicting experimental evidences do exist as to the effectively viable utilization of long chain triglycerides. Supposedly, this impaired utilization would be caused by a relative deficiency of carnitine which, in turn, would bring about an impaired mitochondrial oxidation of long chain fatty acids. Further experimental evidences suggest that high doses of medium chain triglycerides administered to experiment animals wherein ketoacidosis had been induced can bring about toxic effects encompassing narcosis. It is, therefore, felt the need of relying on substrates other than those used to-date.

It has now been found that sebacic acid and the aforesaid pharmacologically acceptable derivatives thereof are an excellent substrate for manufacturing compositions suitable for enteral and parenteral nutrition, which do not present the drawbacks of the known substrates.

The present invention provides, therefore, pharmaceutical compositions suited for enteral and parenteral administration characterized in that they comprise, as active principle, sebacic acid or a derivative thereof. Particularly, the sebacic acid derivative is selected from the pharmacologically acceptable sebacic acid salts, the sebacic acid triglyceride and the pharmacologically acceptable salts of the sebacic acid triglyceride. Preferably, the pharmacologically acceptable salt of sebacic acid or sebacic acid triglyceride is selected from the sodium and the potassium salts.

The pharmaceutical compositions, when they are formulated as aqueous solutions, comprise from 0.2 to 0.6 moles/liter of a pharmacologically acceptable salt of sebacic acid or from 0.2 to 1 moles/liter of sebacic acid triglyceride or a pharmacologically acceptable salt of sebacic acid triglyceride. Preferably, they comprise 0.5 moles/liter of salt, triglyceride or triglyceride salt of sebacic acid.

The orally administrable compositions in unit dosage form, e.g. capsules, comprise from 0.5 to 1.5 grams of salt, trigliceride or triglyceride salt of sebacic acid.

Sodium and potassium sebacate are prepared by neutralization of sebacic acid (C10) with NaOH or KOH (molar ratio $OH^-$:C10 2:1).

In order to prepare the sodium and potassium salts of sebacic acid triglyceride, sebacic acid is added to thionyl chloride (b.p. 79° C.) in dioxane freshly distilled over lithium and aluminum hydroxide (molar ratio C10:thionyl chloride 1:2), keeping the resulting mixture at the reflux temperature for 5-6 hours in the presence of cesium chloride as catalyst. By removing dioxane under vacuum the acid chloride of sebacic acid is obtained.

The triglyceride is dissolved in distilled water in the presence of small amounts of magnesium as catalyst and NaOH to maintain the solution pH at about 8 and to form, by reacting with HCl that frees from the esterification reaction, NaCl and $H_2O$ when C10 acid chloride is added to the reaction mixture.

To this aqueous solution, an excess amount of C10 acid chloride dissolved in dioxane (5-8 times the glycerol amount, lest the polymerization of the compound thus formed may occur) is slowly added in a nitrogen atmosphere, while taking care to maintain a basic pH by addition of small NaOH portions. The reaction reaches completion in about 30 minutes, if small amounts of reagents are used. Double distilled water is then added in order to obtain a clear solution and the excess of free acids is removed via three extractions with diethyl ether. Traces of ether dissolved in the solution are removed by bubbling nitrogen therein. Finally, the solution is dialyzed against double distilled water for 24 hours, in order to remove the alkaline metal chloride.

Neither sebacic acid nor its derivatives according to the present invention are toxic.

Acute toxicity tests following oral and intraperitoneal administration of disodium sebacate to Wistar rats (128 rats, 64 male and 64 female) and New Zealand rabbits (128 rabbits, 64 male and 64 female) did not allow $LD_{50}$ to be assessed. Similarly, subacute and chronic toxicities were studied in 40 rats (20 male and 20 female) and 40 rabbits (20 male and 20 female) that had been administered sebacic acid formulated into pellets. No significant difference in biological parameters (haematic values, growing curves, the taking of histologic samples from various organs) was detected in the treated animals compared with the control animals. Moreover, fetal toxicity tests, teratogenesis tests and neonatal toxicity tests performed on rats and rabbits did not allow any toxicity effect to be detected. In particular, no teratogenic effect was ever noticed whilst fetal development was absolutely normal.

Sodium and potassium sebacates, too, do not exhibit particular acute or chronic toxic effects in rats and rabbits. Since the same death rate is found in animals administered saline only containing a high sodium amount, it is apparent that toxicity is to be attributed to sodium.

Finally, alkaline metal sebacates are not toxic towards fetuses and newly-born animals even when the mothers are administered high doses of sebacate during pregnancy.

In man, too, no toxic effects were found even following long-term treatment.

On the other hand, sebacic acid and its derivatives are easily metabolized since they are beta-oxidized and CoA-activated not only in mitochondria, as it occurs for the fatty acids used to-date, but also in peroxisomes down to the level of C6 that, freed in cytoplasm, can enter the mitochondria via a carnitine acyl transferase-independent pathway.

This particular metabolic pathway makes these compounds highly suited in sepsis conditions, since their metabolism is influenced to a lesser degree by a carnitine decrease.

Moreover, in comparison with the fatty substrates in use to-date, the compounds of the present invention exhibit a high molar ratio $ATP/CO_2$, i.e. a higher energy output with an attendant lower $CO_2$ production. This is particularly advantageous in patients presenting alterations in respiratory parameters.

In those cases wherein the administration of a reduced sodium amount is of major importance, the triglyceride salt will be the compound of choice since it contains half the sodium amount of the corresponding sebacate.

The effectiveness and advantages of the substrates for enteral and parenteral nutrition according to the present invention were assessed by several clinical trials. One of these is hereinbelow briefly outlined.

Two groups of healthy male volunteers were admitted to the trial. The first group, composed of 6 subjects, received 1000 mg sebacate as a bolus; 6 other subjects (second group) received 10 g sebacate dissolved in 500 ml of double distilled water at an infusion rate of 3.33 g/h over 3 hours. The serum sebacate data for each subject were analysed by computer, using biexponential fit corresponding to a 2-compartment open model. The distribution half-life ($t_{\frac{1}{2}}$) was $0.34 \pm 0.06$ h and the elimination phase was rather rapid ($Ke = 2.10 \pm 0.38$ $h^{-1}$); the volume of the central compartment was $2.79 \pm 0.54$ l and the volume of tissue compartment $3.72 \pm 0.14$ l. These data showed a good tissue fixation of sebacate. The plasma clearance was evaluated to be $5.96 \pm 2.19$ l/h and the renal clearance $19.22 \pm 10.69$ l/h, indicating that a tubular secretion of sebacic acid had taken place. The serum concentration of sebacate raised to its peak value at the end of the infusion (180 min) and corresponded to $480.50 \pm 43.02$ μg/ml.

Respiratory and metabolic parameters were evaluated by indirect calorimetry from the beginning of the infusion for 210 minutes. The $O_2$ consumption ($VO_2$ ml/min/m$^2$) remained essentially unchanged throughout the experiment (from $154.3 \pm 28.3$ at time 0 to $155.3 \pm 39.5$ at time 180 min). The $CO_2$ production ($VCO_2$ ml/min/m$^2$) decreased below basal values ($147.7 \pm 27.3$) up to $123.7 \pm 25.0$ at the end of the infusion. Thus respiratory quotient (RQ) decreased significantly (from $0.96 \pm 0.04$ to $0.81 \pm 0.06$) and the percent of calories derived from lipids increased during and after the infusion (from $-0.13 \pm 13.3$ to $52.1 \pm 26.2$). Metabolic rate (MR Kcal/h/m$^2$) remained constant during the entire study period.

In this trial, the urinary excretion of sebacic acid and its products of beta-oxidation (suberic (C8) and adipic ((C6) acids) was found to be low (totaling less than 16% of the administered dose). The energy production was high (6.64 Kcal/g), sebacic acid being completely oxidized in the body to $CO_2$ and $H_2O$.

I claim:

1. A method of providing nutrition to a patient in need thereof comprising administering an effective amount of sebacic acid or a pharmacologically acceptable derivative thereof.

2. The method according to claim 1, wherein said pharmacologically acceptable derivative of sebacic acid is selected from the group comprising sebacic acid, sebacic acid triglyceride and pharmaceutically acceptable salts of sebacic acid triglyceride.

3. The method according to claim 2, wherein the pharmaceutically acceptable salt of sebacic acid or sebacic acid triglyceride is selected from the group consisting of sodium salt and potassium salt.

4. The method according to claim 1, wherein said sebacic acid or pharmacologically acceptable derivative thereof is administered as an aqueous solution comprising from 0.2 to 1 mol/liter of sebacic acid triglyceride or a pharmaceutically acceptable salt of sebacic acid triglyceride.

5. The method according to claim 4, wherein said sebacic acid or pharmacologically acceptable derivative thereof is administered as an aqueous solution comprising about 0.5 moles/liter of sebacic acid triglyceride or a pharmaceutically acceptable salt of sebacic acid triglyceride.

6. The method according to claim 1, wherein said sebacic acid or pharmacologically acceptable derivative thereof is suitable for oral administration and wherein said effective amount comprises from 0.5 to 1.5 grams of sebacic acid triglyceride or a pharmaceutically acceptable salt of sebacic acid triglyceride.

7. The method according to claim 6, wherein said sebacic acid or pharmacologically acceptable derivative thereof is formulated as a capsule.

8. The method according to claim 1, wherein the pharmacologically acceptable derivative is an alkaline metal salt of sebacic acid triglyceride.

* * * * *